United States Patent [19]

Okamoto et al.

[11] Patent Number: 4,861,872
[45] Date of Patent: Aug. 29, 1989

[54] ALKYL-PHENYLCARBAMATE DERIVATIVE OF POLYSACCHARIDE

[75] Inventors: Yoshio Okamoto, Amagasaki; Koichi Hatada, Ikeda, both of Japan

[73] Assignee: Daicel Chemical Industries, Ltd., Sakai, Japan

[21] Appl. No.: 160,539

[22] Filed: Feb. 26, 1988

Related U.S. Application Data

[63] Continuation-in-part of Ser. No. 24,741, Mar. 11, 1987.

[30] Foreign Application Priority Data

Mar. 20, 1986 [JP] Japan .................. 61-62828
Mar. 4, 1987 [JP] Japan .................. 62-49144
Mar. 20, 1987 [JP] Japan .................. 62-65989
Feb. 8, 1988 [JP] Japan .................. 63-26995

[51] Int. Cl.$^4$ ............ C08B 15/06; C08B 33/00; C08B 37/02; C08B 37/08
[52] U.S. Cl. ............ 536/18.7; 106/162; 106/163.1; 106/210; 106/205; 106/208; 210/656; 536/20; 536/30; 536/45; 536/51
[58] Field of Search .......... 210/656; 536/18.7, 20, 536/30, 51, 45; 106/162, 163.1, 210, 205, 208

[56] References Cited

FOREIGN PATENT DOCUMENTS 0238044 3/1987
2101630 7/1971 France.

OTHER PUBLICATIONS

McCormick et al., "Homogeneous Solution Reactions of Cellulose, Chitin, and Other Polysaccharides", 1980 American Chemical Society, pp. 372–380.

Yoshio Okamoto et al, "Controlled Chiral Recognition of Cellulose Triphenylcarbamate Derivatives Supported on Silica Gel", 1986 Journal of Chromatography, pp. 173–186.

*Primary Examiner*—Ronald W. Griffin
*Attorney, Agent, or Firm*—Flynn, Thiel, Boutell & Tanis

[57] ABSTRACT

An alkyl-phenylcarbamate derivative of a polysaccharide has in 80 to 100 percent of hydrogen atoms of the amino and hydroxyl groups an alkylphenyl-carbamoyl group having the formula (I):

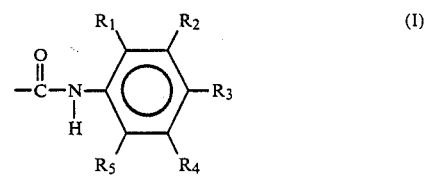

in which (1) at least one of $R_1$ to $R_5$ is a straight alkyl having 4 to 8 or a branched alkyl having 3 to 8 carbon atoms or at least two of $R_1$ to $R_5$ each are a straight alkyl having 1 to 3 when the polysaccharide is cellulose; (2) at least one of $R_1$ to $R_5$ is a straight alkyl having 1 to 8 carbon atoms or a branched alkyl having 3 to 8 carbon atoms when the polysaccharide is any one other than cellulose; and the other(s) of $R_1$ to $R_5$ is hydrogen. It is useful to optical separation of a racemic mixture.

17 Claims, 1 Drawing Sheet

ALKYL-PHENYLCARBAMATE DERIVATIVE OF POLYSACCHARIDE

CROSS-REFERENCE TO RELATED APPLICATION

This is a continuation-in-part of Ser. No. 024,741, filed Mar. 11, 1987.

FIELD OF THE INVENTION

The present invention relates to an alkyl-substituted phenylcarbamate derivative of a polysaccharide, which is a novel polymer very valuable as a functional material.

DESCRIPTION OF THE PRIOR ART

It is known that a packing for a liquid chromatographic column comprising cellulose trisphenylcarbamate as the stationary phase has an excellent optical resolving capacity (Okamoto, Hatakeda et al., Journal of the American Chemical Society, 106, 5357 (1984)).

SUMMARY OF THE INVENTION

We have made research on carbamate derivatives of polysaccharides other than cellulose and, as the result, have found that an alkyl-substituted phenylcarbamate derivative of a polysaccharide such as cellulose can be easily prepared and has an excellent chiral discriminating power. We have now completed the present invention based on this finding.

The invention provides an alkyl-phenylcarbamate derivative of a polysaccharide 80 to 100 percent of hydrogen in the amino and hydroxyl groups of which have been substituted by an alkylphenyl-carbamoyl group having the formula (I):

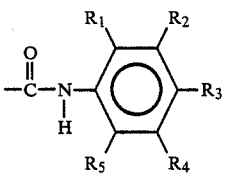

(I)

in which (1) at least one of R1 to R5 is a straight alkyl having 4 to 8 or a branched alkyl having 3 to 8 carbon atoms or at least two of R1 to R5 each are a straight alkyl having 1 to 3 when the polysaccharide is cellulose; (2) at least one of R1 to R5 is a straight alkyl having 1 to 8 carbon atoms or a branched alkyl having 3 to 8 carbon atoms when the polysaccharide is any one other than cellulose; and the other(s) of R1 to R5 is hydrogen.

The alkylphenyl carbamate of a polysaccharide according to the invention includes the following three embodiments:

(a) the polysaccharide is cellulose and at least two of R1 to R5 each are a straight alkyl having 1 to 3 carbon atoms;

(b) the polysaccharide is cellulose and at least one of R1 to R5 is a straight alkyl having 4 to 8 or a branched alkyl having 3 to 8; and (c) the polysaccharide is any polysaccharide other than cellulose and at least one of R1 to R5 is a straight alkyl having 1 to 8 or a branched alkyl having 3 to 8 carbon atoms.

The invention includes the following two embodiments. One cellulose type carbamate derivative comprises repeating constitutional units represented by the following general formula:

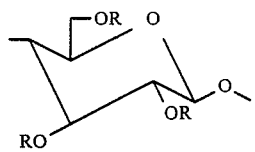

wherein 80 to 100% of R's are

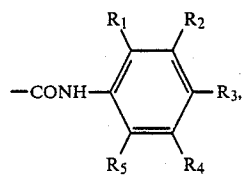

and at least one of $R_1$ to $R_5$ represents a 4 to 8C straight-chain alkyl group or a 3 to 8C branched alkyl group. The is an alkyl-substituted phenyl carbamate derivative of a polysaccharide (excluding cellulose) wherein 80 to 100% of the H's of the hydroxyl groups and the amino groups are substituted by groups represented by the following general formula:

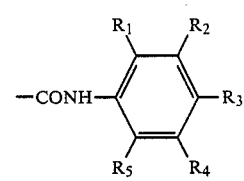

wherein at least one of $R_1$ to $R_5$ represents a 3 to 8C branched alkyl group.

The former of the above shown two embodiments corresponds to the embodiment (b). The latter is included in the embodiment (c).

It is preferred in the above shown embodiments (a) and (b) that the carbamoyl is 3,4-dimethyl-phenyl-carbamoyl, 3,5-dimethyl-phenyl-carbamoyl, p-n-pentyl-phenyl-carbamoyl or p-tert-butyl-phenyl-carbamoyl.

A preferable polysaccharide includes amylose, starch, chitosan, dextran and xylan.

It is preferred in the above shown embodiment (c) that the alkyl-phenyl-carbamoyl is 3,5-dimethylphenyl-carbamoyl, 4-methylphenyl-carbamoyl or p-tert.-butyl-phenyl-carbamoyl, The invention moreover provides a separating agent comprising the above defined alkylphenyl carbamate of a polysaccharide. It may further comprises a carrier. The agent serves to obtain, from a racemic mixture of optical isomers, a pure optical isomer or a mixture of optical isomers having a higher enantiomeric content than the starting mixture by bringing the mixture into contact therewith.

The invention provides the optical resolution method or the optical separation method with an unexpected improvement in view of the capacity factor, the separation factor and the resolution.

Any of synthetic polysaccharides, natural polysaccharides and modified natural polysaccharides which are optically active can be used as the polysaccharide in the present invention, but a polysaccharide having a high regularity in the bonding manner is preferred. For example, there can be mentioned α-1,4-glucan (amylose and amylopectin), α-1,6-glucan (dextran), β-1,6-glucan (pustulan), β-1,3-glucan (such as curdlan or schizophyllan), α-1,3-glucan, β-1,2-glucan (crown gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose and alginic acid. Moreover, starch containing amylose is included. Amylose, β-1,4-chitosan, chitin, β-1,4-mannan, β-1,4-xylan, inulin and curdlan are especially preferred, because polysaccharides having a high purity can be easily obtained therefrom.

The number-averaged degree of polymerization (the average number of pyranose or furanose rings contained in one molecule) ranges from 2 to 1,000, preferably from 5, more preferably from 10. In view of the easiness of handling, it is preferred that it is not larger than 500.

In the formula (I), an alkyl having 1 to 4 carbon atoms may be substituted for R1 to R5 in addition to the above shown specific alkyl groups. The alkylphenyl carbamate of a polysaccharide according to the invention may have terminal groups of hydrogen or a usual group of the polysaccharide.

The reaction ordinarily adopted for forming a urethane from an alcohol and an isocyanate can be directly applied to the synthesis of the carbamate derivative of the present invention. For example, the carbamate derivative of the present invention can be synthesized by reacting a corresponding polysaccharide with a corresponding isocyanate in an appropriate solvent in the presence of a Lewis base such as a tertiary amine or a Lewis acid such as a tin compound as the catalyst. Furthermore, the isocyanate can be easily synthesized by reacting an amino group of a corresponding aniline derivative with phosgene.

When the polysaccharide carbamate derivative of the present invention is used as the separating agent for separating a compound or its optical isomer, there may be generally adopted chromatographic methods such as gas chromatography, liquid chromatography and thin-layer chromatography. Furthermore, the polysaccharide carbamate derivative of the present invention can be applied to the separation method using a membrane.

When the polysaccharide carbamate derivative of the present invention is used for liquid chromatography, the derivative is generally packed in the powdery form into a column, and it is preferred that the derivative be pulverized or formed into beads and that obtained particles be porous. In order to improve the pressure resistance of the separating agent, prevent swelling or shrinkage caused by solvent substitution and increase the number of theoretical plates, it is preferred that the polysaccharide be supported on a carrier.

When the polysaccharide is used as the powder, it is preferred that the particle size or carrier size be 1 μm to 1 mm, especially 1 to 300 μm, preferred size differs to some extent acording to the size of the column. It is preferred that the carrier be porous, and average pore size is 10 Å to 100 μm, preferably 50 to 50000 Å. The amount of the polysaccharide carbamate derivative supported on the carrrier is 1 to 100% by weight, preferably 5 to 50% by weight, based on the carrier.

Either a chemical method or a physical method can be adopted for supporting the polysaccharide carbamate derivative on the carrier. As the physical method, there can be mentioned a method in which the polysaccharide carbamate derivative is dissolved in a solvent capable of dissolving the derivative therein, the solution is sufficiently mixed with the carrier and the solvent is distilled under reduced pressure or heating or in an air flow, and a method in which the polysaccharide carbamate derivative is dissolved in a solvent capable of dissolving the derivative therein, the solution is sufficiently mixed with the carrier and the mixture is dispersed in a solvent incapable of dissolving the derivative therein to diffuse the former solvent. The obtained separating agent is subjected to an appropriate post-treatment such as heating, addition of a solvent or washing to increase the separating capacity.

A porous organic carrier or a porous inorganic carrier can be used as the carrier, and a porous inorganic carrier is preferred. As suitable examples of the porous organic there can be mentioned polystyrene, polyacrylamide and polyacrylate, and as suitable examples of the porous inorganic carrier, there can be mentioned silica, alumina, magnesia, glass, kaolin, titanium oxide and silicate. The surface of the carrier may be treated to improve the affinity with the polysaccharide carbamate derivative or the surface characteristics of the carrier. As the surface treatment method, there can be mentioned a silane treatment using an organic silane compound and a plasma polymerization surface treatment.

The kihd of the developing solvent for liquid chromatography or thin-layer chromatography is not particularly critical, so far as it neither dissolves the polysaccharide carbamate derivative nor reacts therewith. When the polysaccharide derivative is chemically bonded with the carrier or is insolubilized by crosslinking, any developing solvent can be used, so far as it does not react with the polysaccharide carbamate derivative.

In case of thin-layer chromatography, a layer of the separating agent composed of particles having a size of 0.1 μm to 0.1 mm and, if necessary, a small amount of a binder, which has a thickness of 0.1 to 100 mm, is formed on a supporting plate.

In the membrane separation method, the separating agent is formed into a hollow yarn or film and is used in this form.

The polysaccharide carbamate derivative of the present invention is very valuable as a functional material and is especially effective for separation of various compounds, and the polysaccharide carbamate derivative is particularly effective for separation of optical isomers, which is difficult according to the conventional technique, that is, as a packing for the optical resolution.

Figure 1:
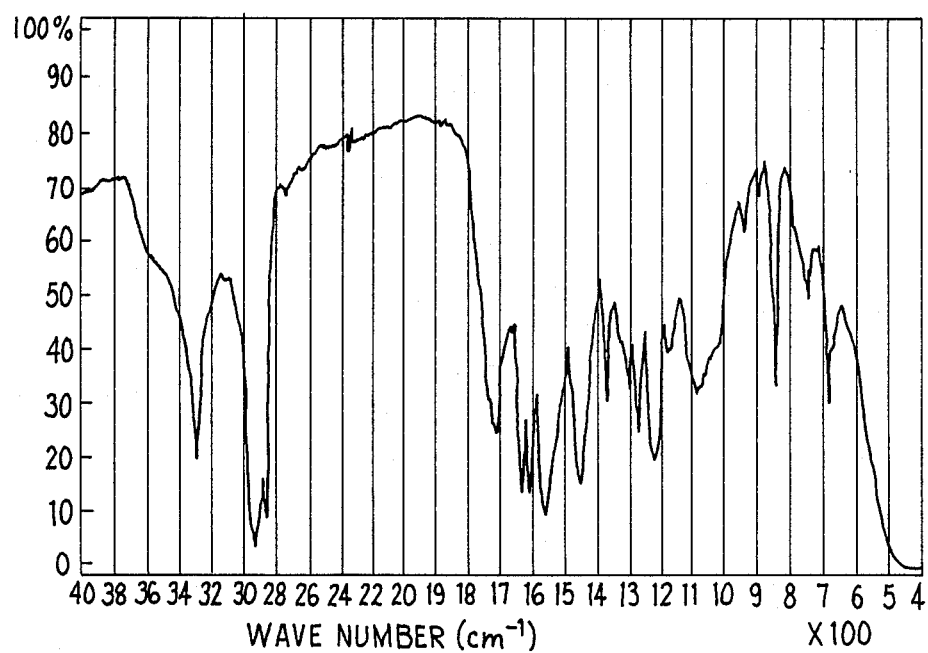
FIG. 1 shows an infra-red spectrum of the product obtained in Example 3.

The present invention will now be described in detail with reference to the following examples that by no means limit the scope of the invention.

The definitions of the terms used in the examples are as follows:

$$\text{Capacity factor } (k') = \frac{\left(\begin{array}{c}\text{(retention time of} \\ \text{entantiomer)}\end{array} - \begin{array}{c}\text{(dead} \\ \text{time)}\end{array}\right)}{\text{(dead time)}}$$

$$\text{Separation factor } (\alpha) = \frac{\text{capacity factor of more strongly adsorbed enantiomer}}{\text{capacity factor of more weakly adsorbed enantiomer}}$$

$$\text{Resolution } (Rs) = \frac{2 \times (\text{distance between peaks of more strongly adsorbed and more weakly adsorbed enantiomers})}{\text{sum of band widths of both peaks}}$$

EXAMPLE 1

Synthesis of amylose tris(3,5-dimethylphenyl-carbamate)

1.0 g of amylose (having a molecular weight of about 16,000) was dried in vacuo and 50 ml of dry pyridine was added thereto. The mixture was stirred. 4.0 ml of 3,5-dimethylphenyl isocyanate was added thereto and the obtained mixture was heated with stirring at 100° C. in a nitrogen current for 22 hours. The reaction mixture was transferred into methanol to cause precipitation, and the precipitate was collected on a glass filter. The amount of obtained amylose tris(3,5-dimethylphenyl-carbamate) was 2.465 g (the yield was 66.4%).

Elementary analysis was carried out on the product obtained, and the result is shown hereinunder.

|  | C | H | N |
|---|---|---|---|
| Measured values (%) | 65.20 | 6.17 | 6.93 |
| Theoretical values (%) | 65.66 | 6.18 | 6.70 |

APPLICATION EXAMPLE 1

Amylose tris(3,5-dimethylphenylcarbamate) obtained in Example 1 was supported on a silica gel (Lichrospher SI4000 supplied by E. Merk, 10 μm), and the supported amylose carbamate derivative was packed in a stainless steel column having a length of 25 cm and an inner diameter of 0.46 cm. Optical resolution of various racemic compounds shown in Table 1 was carried out. Good results were obtained as shown in Table 1.

A 9:1 mixed solvent of hexane/2-propanol was used as the solvent. In this table, $k'_1$ represents the capacity factor of the enantiomer first eluted and the parenthesized symbol indicates the optical rotation, while $\alpha$ represents the separation factor and Rs indicates the resolution.

TABLE 1

| racemate*[1] | $k'_1$ | $\alpha$ | Rs |
|---|---|---|---|
| Benzoin | 3.14 (+) | 1.21 | 2.07 |
| Trans-stilbene oxide | 0.42 (+) | 3.40 | 7.88 |
| 2,2-dihydroxy 6,6'-dimethylbiphenyl | 2.46 (−) | 2.11 | 6.38 |
| 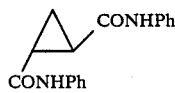 | 3.25 (+) | 2.01 | 3.59 |
| 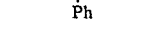 | 2.65 (+) | 1.98 | 5.48 |
| 2,2,2-trifluoro-1-(9-anthryl) ethanol | 1.30 (+) | 1.15 | 0.75 |

TABLE 1-continued

| racemate*[1] | $k'_1$ | $\alpha$ | Rs |
|---|---|---|---|
| Troger's base | 0.53 (+) | 1.58 | 2.30 |

Note
*[1]Ph indicates a phenyl group.

EXAMPLE 2

Starch 3,5-dimethylphenylcarbamate derivative was obtained in the same manner as described in Example 1 except that starch was used instead of amylose. The yield of pyridine soluble portion is 14%, residue is insoluble material.

Optical resolution of various racemic compounds was carried otu as in Application Example 1 by using the obtained carbamate derivative. Good results are similarly otained.

TABLE 2

| racemate*[1] | $k'_1$*[2] | $\alpha$*[2] | Rs*[2] |
|---|---|---|---|
| 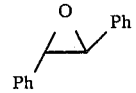 | 0.22(+) | ~1 | |
| 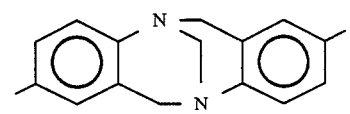 | 0.30(+) | ~1 | |
| 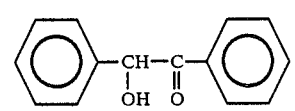 | 1.73(−) | 1.07 | |
| Tr—CH—OH<br>        \|<br>        Ph | 0.56(+) | 1.27 | |
| 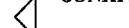 | 0.90(−) | 1.33 | 1.10 |
|  | 1.31(−) | 1.17 | 0.74 |
|  | 0.53(−) | 1.10 | |
|  | 0.65(−) | 1.11 | 0.75 |
| Co(acac)₃ | 4.90(+) | ~1 | |

TABLE 2-continued

| racemate[*1] | $k'_1$[*2] | $\alpha$[*2] | $R_s$[*2] |
|---|---|---|---|
| Ph-Ph-Ph-CH(CF₃)-OH (tritylphenyl structure with CH-OH, CF₃) | 1.49(−) | 1.15 | 0.81 |

Note
[*1] Rh indicates phenyl group.
Tr indicates trityl group ((Ph)₃C—).
acac indicates acetylacetonate group.
[*2] $k'_1$, $\alpha$, $R_s$ indicate the same meaning as in Table 1.

EXAMPLE 3

Synthesis of chitosantris(3,5-dimethylphenyl-carbamate)

0.801 g of chitosan, 50 ml of pyridine, and 5.5 ml of 3,5-dimethylphenyl isocyanate were heated under reflux in a nitrogen gas flow with stirring, the reaction was continued for 43.5 hrs. The reaction solution was entirely poured into methanol, the precipitate was collected on a glass filter followed by washing with methanol and vacuum drying at 40° C. for 5 hrs. and 3.418 g of the product of chitosantris-(3,5-dimethylphenylcarbamate) was obtained.

The result of elementary analysis on the obtained product (soluble portion in $CHCl_3:CF_3CH_2OH$ (9:1)) is shown hereinunder.

|  | C | H | N |
|---|---|---|---|
| Measured values (%) | 68.70 | 6.68 | 9.44 |
| Theoretical values (%) | 68.77 | 6.35 | 9.30 |

Figure 2:
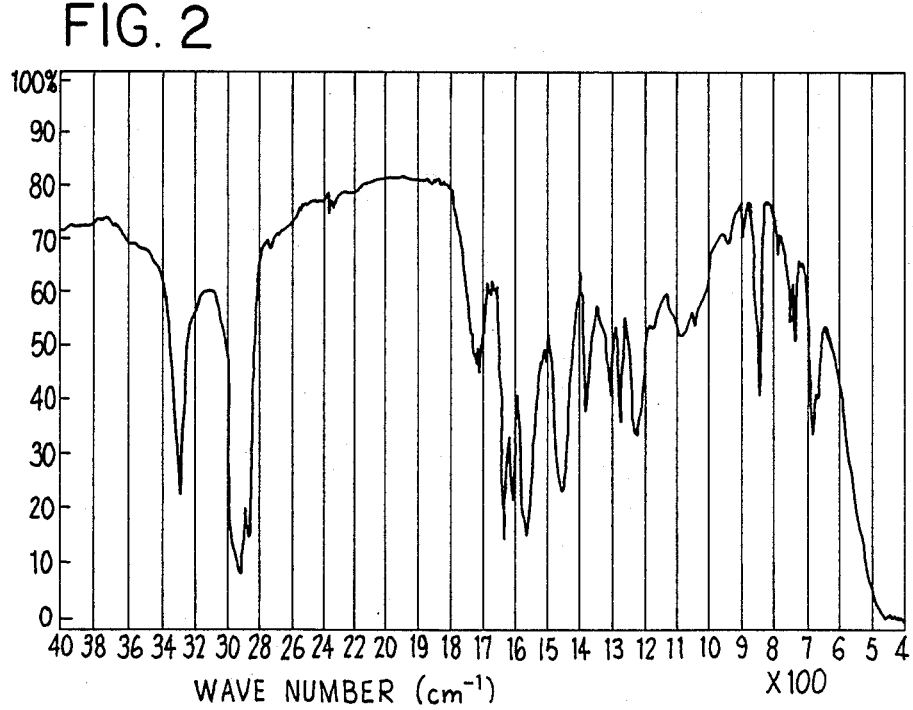
FIG. 2 shows an infrared spectrum of soluble portion in $CHCl_3:CF_3CH_2OH$ (9:1) obtained in Example 3.

The infra-red absorption spectrum of obtained product is shown in FIG. 1 and of soluble portion in $CHCl_3:CF_3CH_2OH$ (9:1) is shown in FIG. 2.

APPLICATION EXAMPLE 2

The product obtained in Example 3 is insoluble in the solvent used usually for supporting (chloroform, tetrahydrofuran, dimethylacetoamide, etc.). 0.625 g of soluble portion from the obtained product was dissolved in 12 ml of hot pyridine at approximately 100° C., and the solution was supported on 2.60 g of silica gel (3-aminotriethoxysilane-treated Lichrospher SI-1000 supplied by E. Merk).

Packing prepared as mentioned above was charged in a column with a length of 25 cm and an inside diameter of 0.46 cm. Optical resolution of various racemic compounds shown in Table 2 was carried out using hexane/2-propanol (90/10) as the eluent with a flow rate of 0.5 ml/min at a temperature of 25° C., and good results were obtained as shown in Table 2.

EXAMPLE 4

Synthesis of amylosetris(4-methylphenylcarbamate)

0.800 g (4.93 m mol) of amylose, 5.07 g (38.1 m mol) of p-toluylisocyanate, and 40 ml of pyridine were heated with stirring for 24 hrs. at 100° C., and then poured into 400 ml of methanol. Obtained precipitate was collected on a glass filter followed by washing with methanol and vacuum drying at 60° C. for 3 hrs., and 2.38 g (yield 85.9%) of amylosetris(4-methylphenylcarbamate) was obtained.

The result of elementary analysis is shown hereinunder.

|  | C | H | N |
|---|---|---|---|
| Measured values (%) | 62.79 | 5.46 | 7.39 |
| Theoretical values (%) | 64.16 | 5.56 | 7.48 |

EXAMPLE 5

Synthesis of dextrantris(3,5-dimethylphenyl-carbamate)

1.00 g (6.17 m mol) of dextran, 30 ml of N,N-dimethylacetamide, and 1.5 g of lithium chloride were heated with stirring for 30 min at 100° C. to dissolve dextran. Into the solution 8.63 g (58.7 m mol) of 3,5-dimethylphenylisocyanate and 2.0 ml of pyridine were added and heated with stirring for 27 hrs. at 100° C., and then poured into 1.5 liter of methanol. Obtained precipitate was collected on a glass filter followed by washing with methanol and vacuum drying at 40° C. for 2 hrs. to obtain 2.49 g (yield 66.6%) of dextrantris(3,5-dimethylphenylcarbamate). The result of elementary analysis is shown hereinunder.

|  | C | H | N |
|---|---|---|---|
| Measured values (%) | 64.55 | 6.17 | 6.78 |
| Theoretical values (%) | 65.66 | 6.18 | 6.70 |

APPLICATION EXAMPLE 3

Amylosetris(4-methylphenylcarbamate) obtained in Example 4 was supported on silica gel (Lichrospher SI 4000 supplied by E. Merk, 10 μm) treated with 3-aminopropyltriethoxysilane, and charged in a stainless steel column with a length of 25 cm an inside diameter of 0.46 cm (this column is referred as column 1 hereinafter).

Similarly, silica gel which supported dextrantris(3,5-dimethylphenylcarbamate) was charged in a column (this column is referred as column 2 hereinafter).

Optical resolution of various racemic compounds shown in Table 3 was carried out on these columns using hexane/2-propanol (90/10) a the eluent with a flow rate of 0.5 ml/min at a temperature of 25° C. Good results were obtained as shown in Table 3.

TABLE 3

| racemate[*1] | Column 1 $\alpha$[*2] | Column 2 $\alpha$[*2] |
|---|---|---|
| Ph₃C—CH(Ph)—OH | 1.57 (+) | 1.57 (+) |
| Troger's base | — | 1.26 (+) |
| Trans-stylbeneoxide | 1.38 (+) | — |
| 2,2'-dihydroxy-6,6'-dimethylbiphenyl | 1.54 (−) | — |
| cyclopropane-CONHPh/CONHPh | 1.44 (+) | 1.35 (+) |

Note
[*1] Rh indicates phenyl group.
[*2] $\alpha$ indicates separation coefficient and inclusion in ( ) indicates the optical rotation.

EXAMPLE 6

Syntehsis of xylanbis (3,5-dimethylphenylcarbamate)

50 ml of pyridine and 3.3 ml (22 m mol) of 3,5-dimethylphenylisocyanate were added to 1.00 g (6.40 m, mol) of xylan which was dryed previously in an Abderhalden's dryer for one day, and heated with stirring in nitrogen for 26 hrs. at 100° C. After the presence of isocyanate was checked in the reaction solution, the solution was poured into 500 ml of methanol, obtained brown precipitate was collected on a glass filter followed by washing with methanol, vacuum drying in a desiccator, and additional vacuum drying for 6 hrs. at a constant temperature of 50° C. The yield was 2.68 g (98.2%).

The result of elementary analysis of obtained product was shown hereinunder.

|  | C | H | N |
|---|---|---|---|
| Measured values (%) | 63.95 | 6.09 | 6.60 |
| Theoretical values (%) | 64.57 | 6.14 | 6.57 |

APPLICATION EXAMPLE 4

0.675 g of xylantis(3,5-dimethylphenylcarbamate) obtained in Example 6 was dissolved in 12 ml of chloroform, and treated four times parceling off into four lots on 2.70 g of silica gel (Lichrospher SI 4000 supplied by E. Merk, 10 μm) treated with 3-aminopropyltriethoxysilan to be supported thereon. After classification in hexane/2-propanol (90/10) by particle diameter, the silica gel was dispersed in hexane/liquid paraffin (2/1), charged in a column with a length of 25 cm and an inside diameter of 0.46 cm and the column was used for optical resolution.

Optical resolution of various racemic compounds shown in Table 4 was carried out on this column using hexan/2-propanol (90/10) as the eluent with a flow rate of 0.5 ml/min at a temperature of 25° C. Good results were obtained as shown in Table 4.

TABLE 4

| racemate | $k'_1$*2 | $\alpha$*2 | $R_s$*2 |
|---|---|---|---|
| 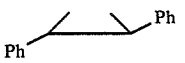 | 0.47 | 1.40 | 1.79(+) |
| 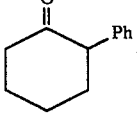 | 1.15 | 1.05 | — |
| 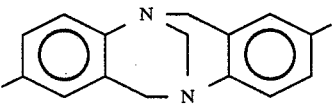 | 0.84 | 1.65 | 2.64(−) |

TABLE 4-continued

| racemate | $k'_1$*2 | $\alpha$*2 | $R_s$*2 |
|---|---|---|---|
| 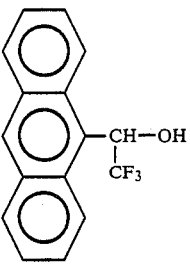 | 1.44 | 1.42 | 2.36(−) |
| Tr—CH—OH<br>    \|<br>    Ph | 1.41 | 1.23 | 1.46(+) |
| 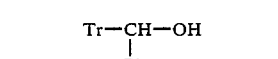 | 2.57 | 1.16 | 172(+) |
| 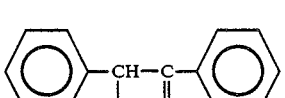 | 1.38 | ~1 | — |
| 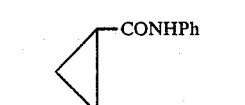 | 1.33 | 1 | — |
| 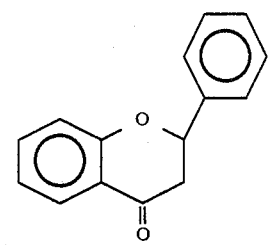 | 2.97 | 1.02 | — |
| Co(acac)₃ | 1.60 | 2.57 | 2.20(+) |

Note
*1Rh, Tr, and acac indicates the same meaning as in Table 2.
*2$k'_1$, α, Rs indicate the same meaning as in Table 1.

EXAMPLE 7

Synthesis of cellulosetris (3,4-dimethylphenyl)carbamate 1 g of fine crystalline cellulose (degree of polymerization of 100, supplied by E Merk), 50 ml of pyridine, and 6.5 ml of 3,4-dimethylphenylisocyanate were mixed with one another and heated for 17 hours at 100° C. Then the reaction mixture was poured into 500 ml of methanol. The obtained precipitates were taken out by filtration and dried.

The yield quantity 3.31 g.
The yield 89%.
The result of elementary analysis

|  | C | H | N |
|---|---|---|---|
| Theoretical values | 65.66 | 6.18 | 6.74 |

|  | C | H | N |
|---|---|---|---|
| Measured values | 63.95 | 6.00 | 6.74 |

EXAMPLE 8

Synthesis of cellulosetris(3,5-dimethylphenyl)carbamate

By the same manner described in Example 7, 1 g of fine crystalline cellulose and 6.5 ml of 3,5-dimethylphenylisocyanate were reacted to form 3,5-dimethylphenylcarbanamate derivative.

The yield quantity: 3.26 g.
The yield 88%.
The result of elementary analysis

|  | C | H | N |
|---|---|---|---|
| Theoretical values | 65.66 | 6.18 | 6.74 |
| Measured values | 64.14 | 6.06 | 6.80 |

APPLICATION EXAMPLE 5

Cellulosetris (3,5-dimethylphenyl)carbamate obtained in Example 8 was adsorbed on silica gel having a particle size of 20 microns and a pore size of 800 angstroms and having beem treated with diphenyldichlorosilane in an amount of 20%, and the packing prepared thereby for optical resolution was used as thin layer. The thin layer was prepared by casting a suspension in which the silica gel was suspended in hexane/carbon tetrachloride (1:21) on a slide glass (7.5×2.5 cm)

Hexane/2-propanol (90:10) was used an as eluent and 1-(9-anthryl)-2,2,2-trifluoroethanol was optical resolved. It took about two and a half minutes that the mobile phase moved to near the top of the thin layer. By repeating this procedure three times the fluorescent spot of racemic compounds was definitely separated. The Rf values are 0.50 and 0.61.

APPLICATION EXAMPLE 6

Cellulosetris(3,5-dimethyphenyl)carbamate obtained in Example 8 was supported on silica gel (Lichrospher SI4000, 10 μm, supplied by E. Merk) a stainless sleel column (length of 25 cm, inside diameter of 0.46 cm) was charged therewith, racemic compounds were subjected to optical resolution to obtain the result shown in Table 5. Hexane/2-Prepanol mixture was used as the solvent. In the table K' represents the retention capacity of enantiomer eluated initially, the inclusion in ( ) represents the rotation thereof. α indicates the separation factor and Rs, the resolution.

TABLE 5

| racemate | resolution result | | |
|---|---|---|---|
|  | k'₁ | α | $R_s$ |
| Ph—CH—C—Ph<br>\|  \|\|<br>OH  O | 2.43(+) | 1.58 | 4.38 |
| (epoxide with two Ph groups) | 0.74(−) | 1.68 | 3.22 |

TABLE 5-continued

| racemate | resolution result | | |
|---|---|---|---|
|  | k'₁ | α | $R_s$ |
| 2,2'-dihydroxy-3,3'-dimethylbiphenyl | 2.36(−) | 1.83 | 4.39 |
| cyclopropane-1,2-bis(CONHPh) | 0.83(+) | 3.17 | 6.17 |
| Ph₃C—CH(OH)—Ph | 1.37(+) | 1.34 | 1.87 |
| 9-anthryl-CH(CF₃)—OH | 2.13(−) | 2.59 | 6.40 |
| diazine derivative | 0.97(+) | 1.32 | 1.92 |
| flavone derivative | 1.47(−) | 1.41 | 3.08 |
| 2-phenylcyclohexanone | 1.47(−) | 1.41 | 3.08 |

EXAMPLE 9

Cellulose tris(4-t-butylphenyl carbamate) was synthesized as follows.

(1) Isocyanating 4-t-butylaniline

While carbon tetrachloride was refluxed, fuming sulfuric acid was added dropwise to evolve phosgene. When the atmosphere in the apparatus was replaced sufficiently with phosgene, a 4-t-butylaniline toluene solution (containing 6.00 g of 4-t-butylaniline in 250 ml of toluene) was added dropwise and the temperature was gradually elevated to allow the reaction to proceed while the toluene was refluxed. Yield: 5.61 g (79.6%).

Then the toluene was removed by atmospheric distillation and then the isocyanate was distilled at 83.2° C./6.0 mmHg.

(2) Synthesizing cellulose tris(4-t-butylphenyl carbamate)

0.59 g of cellulose was stirred in about 80 ml of pyridine at 100° C. for 1 hour, then after 30 ml of the pyridine were distilled off, 2.72 g of 4-t-butylphenyl isocyanato were added, and they were reacted at 100° C. for 19 hours.

The contents were poured into methanol to cause precipitation, and the precipitate was centrifugally separated and dried at 60° C. for 2 hours with the temperature kept constant. Yield: 1.56 g (67.5%).

EXAMPLE 10

Amylose tris(4-t-butylphenyl carbamate) was synthesized as follows.

0.51 g of amylose were stirred in about 75 ml of pyridine at 100° C. for 2 hours, then about 30 ml of the pyridine were distilled off, and after 2.89 g of 4-t-butylphenylisocyanato were added, the reaction was carried out for 20 hours.

The contents were poured into methanol to cause precipitation, and the precipitate was filtered through a glass filter, and was dried at 60° C. for 2 hours with the temperature kept constant. Yield: 1.18 g (55.7%).

The analysis of the compounds in Examples 1 and 2 are shown below.

|  | Elemental analysis figures (%) | | |
|---|---|---|---|
|  | C | H | N |
| Cellulose tris(4-t-butylphenyl carbamate) | 67.09 (68.10) | 7.07 (7.18) | 6.01 (6.11) |
| Amylose tris(4-t-butylphenyl carbamate) | 67.36 (68.10) | 7.20 (7.18) | 5.94 (6.11) |

Figures in parenthesises are theoretical values.

APPLICATION EXAMPLES 7 AND 8

Using the compounds prepared in Examples 9 and 10, separating agents and separating columns were prepared as shown below.

(1) Separating agents

Silica gel (YRK25) having a particle diameter of 7 μm and a pore diameter of 4000 Å whose surfaces have been treated with 3-aminopropyltriethoxysilane was used. About 0.75 g of cellulose tris(4-t-butylphenyl carbamate) and about 0.75 g of amylose tris(4-t-butylphenyl carbamate) were dissolved each in about 10 ml of tetrahydrofuran. Every time when about 3 g of YRK25 were used, about 2.5 ml of each of the tetrahydrofuran solutions was added, followed by shaking well, and after the silica gel was uniformly made wet, the evaporation and vacuum drying (60° C.) were effected. That procedure was repeated to support the whole of each compound.

(2) Separating columns

Each of the separating agents prepared in step (1) was classified by using hexane/2-propanol (90:10), and was loaded into a stainless steel column having a length of 25 cm and an inner diameter of 0.46 cm by the slurry packing method. Mixtures of optical isomers shown in Table 6 were separated by using the thus produced separating columns. The separating conditions and the results are shown in Table 6.

TABLE 6

| racemate | Example 9 | | | Example 10 | | |
|---|---|---|---|---|---|---|
|  | $k_1'$ | α | Rs | $k_1'$ | α | Rs |
| 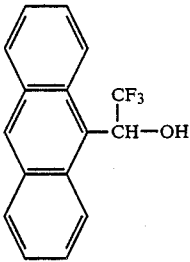 | 1.18(−) | 1.75 | 3.70 | 0.93(−) | 1.12 | |
| 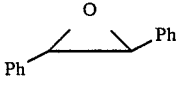 | 0.45(+) | 1.27 | 0.84 | 0.59(−) | ∼1 | |
| Troger base | 1.07(−) | 1.74 | 3.09 | 1.34(+) | 1.32 | 1.64 |
| Co(acac)$_3$ | 0.33(+) | 2.50 | 3.51 | 0.48(−) | ∼1 | |
| 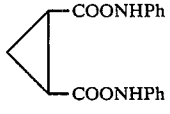 | 1.26(−) | 2.24 | 4.37 | 0.93(+) | 1.16 | |
| 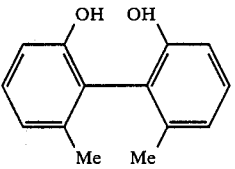 | 1.55(−) | 1.50 | 2.47 | 1.59(−) | 1.08 | |
| 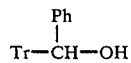 Tr—CH—OH | 0.79(+) | 1.36 | 1.76 | 1.16(+) | 1.14 | 0.88 |

TABLE 6-continued

| racemate | Example 9 | | | Example 10 | | |
|---|---|---|---|---|---|---|
| | $k_1'$ | α | Rs | $k_1'$ | α | Rs |
| 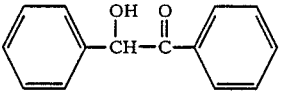 | 2.03(−) | 1.08 | | 3.67(−) | 1.17 | 1.69 |
| 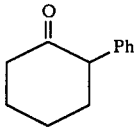 | 1.13(−) | 1.22 | 1.42 | 1.39(+) | 1.43 | 2.40 |
| 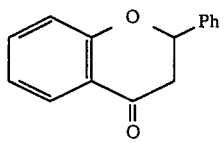 | 1.40(+) | 1.45 | 2.56 | 1.71 | 1.00 | |
|  | 2.14(+) | 1.29 | 1.03 | 0.98 | 1.00 | |
| 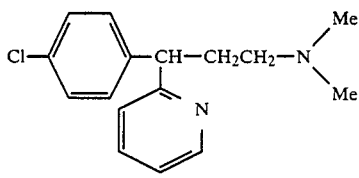 | 0.80(−) | 1.12 | | 1.13(−) | 1.45 | 1.36 |
| EEDQ | 0.73(−) | 1.25* | | 0.35(−) | 1.22 | |
| 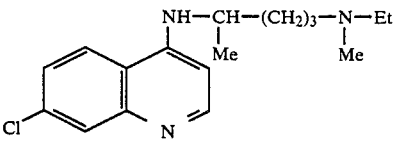 | 3.89(−) | 1.16 | | | | |
| Nicardipine | 8.04(−) | 1.21 | 1.29 | 3.42 | 1.00 | |
| 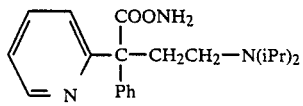 | 3.36(−) | 1.04 | | | | |

Hexane/2-propanol(90:10); 0.5 ml/min; 25° C.
*Hexane/2-propanol(98:2)

EXAMPLE 11

Cellulose tris(4-n-pentylphenyl carbamate) was synthesized as follows.

0.88 g of cellulose was suspended in 40 ml of pyridine, then 4.5 g (1.4 equivalent) of 4-n-pentylphenyl isocyanate were added, and the reaction was carried out at 100° C. for 24 hours. The reaction mixture solution that became homogeneous was poured into 400 ml of methanol to deposit the product. The product was collected on a glass filter, then washed with methanol, and dried in vacuo at 60° C. for 2 hours. Yield: 3.20 g (80.8%).

| | C | H | N |
|---|---|---|---|
| Elemental analysis figures | 67.15% | 7.39% | 5.44% |
| Calculated | 69.11% | 7.60% | 5.76% |

APPLICATION EXAMPLE 9

The optical resoluting ability of the compound obtained in Example 11 was assessed as follows.

0.75 g of the synthesized polysaccharide derivative was dissolved in 15 ml of tetrahydrofuran, and then was supported on 2.98 g of silica gel (that had a particle diameter of 10 μm, and a pore diameter of 4000 A, and had been treated with 3-amyinopropyltriehhoxysilane). The thus obtained separating agent was loaded into a column having a length of 25 cm and an inner diameter of 0.46 cm by the slurry method. The separation test was carried out in the same manner as in Application Example 7. Results are shown in Table 7.

TABLE 7

Optical resolution of cellulose (4-n-pentylphenyl carbamate)

| racemate | k₁' | α | Rs |
|---|---|---|---|
| C₅H₅–CH(O)–CH–C₆H₅ (stilbene oxide) | 0.28 | 1.61 | 1.19 |
| (dibenzyl diamine structure) | 0.98 | 1.19 | |
| phenyl(o-tolyl)(2-pyridyl)methanol | 0.33 | 1.21 | |
| Co(acac)₃ | 0.89 | 1.77 | 2.84 |
| CH₂=C(CH₃)–COO–C(2-pyridyl)(o-tolyl)₂ | 0.42 | ~1 | |
| C₆H₅–CH(OH)CH₃ | 1.56 | 1.06 | |

Eluent liquid: Hexane/2-propanol(98:2) at 0.5 ml per min. at 25° C.

What is claimed is:

1. An alkyl-phenylcarbamate derivative of a polysaccharide 80 to 100 percent of hydrogen in the amino and hydroxyl groups of which have been substituted by an alkylphenylcarbamoyl group having the formula (I):

(structure I: phenyl ring with R1, R2, R3, R4, R5 substituents and –C(=O)–NH– group)

in which (1) at least one of R1 to R5 is a straight alkyl having 4 to 8 carbon atoms or a branched alkyl having 3 to 8 carbon atoms or at least two of R1 to R5 each are a straight alkyl having 1 to 3 carbon atoms when the polysaccharide is cellulose; (2) at least one of R1 to R5 is a straight alkyl having 1 to 8 carbon atoms or a branched alkyl having 3 to 8 carbon atoms when the polysaccharide is any one other than cellulose and dextran; and the other (s) of R1 to R5 is hydrogen.

2. The derivative as claimed in claim 1, in which the polysaccharide is cellulose and at least two of R1 to R5 each are a straight alkyl having 1 to 3 carbon atoms.

3. The derivative as claimed in claim 1, in which the polysaccharide is cellulose and at least one of R1 to R5 is a straight alkyl having 4 to 8 carbon atoms or a branched alkyl having 3 to 8 carbon atoms.

4. The derivative as claimed in claim 1, in which the polysaccharide is any polysaccharide other than cellulose and dextran and at least one of R1 to R5 is a straight alkyl having 1 to 8 carbon atoms or a branched alkyl having 3 to 8 carbon atoms.

5. The derivative as claimed in claim 1, in which the polysaccharide is cellulose and the carbamoyl is 3,4-dimethyl-phenyl-carbamoyl, 3,5-dimethyl-phenyl-carbamoyl, p-n-pentyl-phenyl-carbamoyl or p-tert-butyl-phenyl-carbamoyl.

6. The derivative as claimed in claim 1, in which the polysaccharide is selected from the group consisting of amylose, starch, chitosan, and xylan.

7. The derivative as claimed in claim 1, in which the polysaccharide is any one other than cellulose and dextran and the alkyl-phenyl-carbamoyl is selected from the group consisting of 3,5-dimethylphenyl-carbamoyl, 4-methylphenyl-carbamoyl and p-tert.-butylphenyl-carbamoyl.

8. The derivative as claimed in claim 1, which has a number-average polymerization degree of 2 to 1,000.

9. The derivative as claimed in claim 1, which is in the form of porous particles having a particle size of 1 micron to 1 mm and an average pore size of 10 A to 100 microns.

10. A separating agent which comprises a carrier and 1 to 100 percent by weight, based on the carrier, of the derivative as defined in claim 1.

11. The derivative as claimed in claim 1, which the polysaccharide is any one other than cellulose and dextran and at least one of R1 to R5 is a straight alkyl having 1 to 8 carbon atoms.

12. A method for obtaining, from a racemic mixture of optical isomers, a pure optical isomer or a mixture of optical iosmers having a higher enantiomeric content than the starting mixture by bringing the mixture into contact with the derivative as defined in claim 1.

13. A method as claimed in claim 12, which is conducted by chromatography.

14. A method for obtaining, from a racemic mixing of otpical isomers, a pure optical isomer or a mixture of optical isomers having a higher enantiomeric content than the starting mixture by bringing the mixture into contact with the derivative as defined in claim 9.

15. A method as claimed in claim 14, which is conducted by chromatography.

16. A method for obtaining, from a racemic mixture of optical isomers, a pure optical isomer or a mixture of optical isomers having a higher enantiomeric content than the starting mixture by bringing the mixture into contact with the separating agent as defined in claim 10.

17. A method as claimed in claim 16, which is conducted by chromotography.

* * * * *